United States Patent
Ivanov et al.

(10) Patent No.: US 9,351,091 B2
(45) Date of Patent: May 24, 2016

(54) APPARATUS WITH ADAPTIVE MICROPHONE CONFIGURATION BASED ON SURFACE PROXIMITY, SURFACE TYPE AND MOTION

(71) Applicant: Google Technology Holdings LLC, Mountain View, CA (US)

(72) Inventors: Plamen A Ivanov, Schaumburg, IL (US); Kevin J Bastyr, Milwaukee, WI (US); Joel A Clark, Woodridge, IL (US); Rivanaldo S Oliveira, Grayslake, IL (US); Snehitha Singaraju, Gurnee, IL (US); Jincheng Wu, Naperville, IL (US)

(73) Assignee: Google Technology Holdings LLC, Mountain View, CA (US)

( * ) Notice: Subject to any disclaimer, the term of this patent is extended or adjusted under 35 U.S.C. 154(b) by 109 days.

(21) Appl. No.: 13/955,199

(22) Filed: Jul. 31, 2013

(65) Prior Publication Data

US 2014/0270217 A1   Sep. 18, 2014

Related U.S. Application Data

(60) Provisional application No. 61/827,569, filed on May 25, 2013, provisional application No. 61/776,793, filed on Mar. 12, 2013, provisional application No. 61/798,097, filed on Mar. 15, 2013.

(51) Int. Cl.
*H04B 3/20* (2006.01)
*H04R 29/00* (2006.01)
(Continued)

(52) U.S. Cl.
CPC ............ *H04R 29/005* (2013.01); *G10K 11/178* (2013.01); *H04M 1/6041* (2013.01); *H04R 3/005* (2013.01); *H04M 2250/12* (2013.01); *H04R 2430/20* (2013.01); *H04R 2499/11* (2013.01)

(58) Field of Classification Search
None
See application file for complete search history.

(56) References Cited

U.S. PATENT DOCUMENTS 7,142,678 B2   11/2006   Falcon
7,260,209 B2   8/2007    Harvey et al.
(Continued)

FOREIGN PATENT DOCUMENTS

EP   2278356 A1   1/2011
WO   WO 2009/097407 A1   8/2009

OTHER PUBLICATIONS

European Patent Office, Invitation to Pay Additional Fees and, Where Applicable, Protest Fee in International Patent Application PCT/US2014/016364, May 8, 2014.
(Continued)

*Primary Examiner* — Regina N Holder
(74) *Attorney, Agent, or Firm* — Wolfe-SBMC

(57) ABSTRACT

An apparatus includes a group of microphones and a surface compensator that is operatively coupled to switch logic and to a signal conditioner that provides a control channel to voice recognition logic. The surface compensator may detect surfaces in proximity to the apparatus as well as the surface's acoustic reflectivity or acoustic absorptivity and may accordingly configure the group of microphones including selecting appropriate signal conditioning and beamforming based on the surface acoustic reflectivity or acoustic absorptivity and the orientation of the apparatus. Voice recognition performance is thus improved when microphones are impeded or occluded by proximate surfaces. A group of sensors of the apparatus is used by the surface compensator to detect surfaces and surface type, and to determine apparatus orientation and motion.

20 Claims, 3 Drawing Sheets

(51) Int. Cl.
*G10K 11/178* (2006.01)
*H04R 3/00* (2006.01)
*H04M 1/60* (2006.01)

(56) References Cited

U.S. PATENT DOCUMENTS

| | | |
|---|---|---|
| 2006/0074684 A1 | 4/2006 | Yoshida et al. |
| 2006/0126858 A1* | 6/2006 | Larsen et al. .................. 381/63 |
| 2006/0235688 A1 | 10/2006 | Bicego et al. |
| 2006/0247927 A1 | 11/2006 | Robbins et al. |
| 2009/0209293 A1 | 8/2009 | Louch |
| 2010/0195838 A1 | 8/2010 | Bright |
| 2010/0215184 A1* | 8/2010 | Buck et al. .................... 381/66 |
| 2011/0044474 A1 | 2/2011 | Grover et al. |
| 2011/0077939 A1 | 3/2011 | Jung et al. |
| 2011/0194230 A1 | 8/2011 | Hart et al. |
| 2012/0182539 A1 | 7/2012 | Grokop et al. |
| 2012/0263019 A1 | 10/2012 | Armstong-Muntner |
| 2013/0297926 A1* | 11/2013 | Eaton et al. ................... 713/100 |
| 2013/0332156 A1* | 12/2013 | Tackin et al. .................. 704/226 |

OTHER PUBLICATIONS

Seltzer et al., "Speech Recognizer-Based Microphone Array Processing for Robust Hands-Free Speech Recognition", 2002 IEEE International Conference on Acoustics, Speech, and Signal Processing Proceedings. (ICASSP). Orlando, FL, May 13-17, 2002; [IEEE International Conference on Acoustics, Speech, and Signal Processing (ICASSP)], New York, NY: IEEE, May 13, 2002 pp. I-897-I-900.

Eupopean Patent Office, International Search Report and the Written Opinion of International Application No. PCT/US2014/016364 (Jul. 17, 2015).

"International Search Report and Written Opinion", Application No. PCT/US2014/042325, Nov. 24, 2014, 16 pages.

"Restriction Requirement", U.S. Appl. No. 13/948,189, Mar. 11, 2016, 5 pages.

\* cited by examiner

APPARATUS WITH ADAPTIVE MICROPHONE CONFIGURATION BASED ON SURFACE PROXIMITY, SURFACE TYPE AND MOTION

CROSS-REFERENCE TO RELATED APPLICATIONS

The present application claims priority to U.S. Provisional Patent Application No. 61/827,569, filed May 25, 2013, entitled "VOICE RECOGNITION SYSTEM WITH ADAPTIVE ADJUSTMENT BASED ON SURFACE PROXIMITY, SURFACE TYPE AND MOTION" which is incorporated in its entirety herein, and further claims priority to U.S. Provisional Patent Application No. 61/798,097, filed Mar. 15, 2013, entitled "VOICE RECOGNITION FOR A MOBILE DEVICE," and further claims priority to U.S. Provisional Pat. App. No. 61/776,793, filed Mar. 12, 2013, entitled "VOICE RECOGNITION FOR A MOBILE DEVICE," all of which are assigned to the same assignee as the present application, and all of which are hereby incorporated by reference herein in their entirety.

FIELD OF THE DISCLOSURE

The present disclosure relates generally to mobile devices and more particularly to voice processing and to voice recognition systems for such mobile devices.

BACKGROUND

Mobile devices such as, but not limited to, mobile phones, smart phones, personal digital assistants (PDAs), tablets, laptops or other electronic devices, etc., increasingly include voice recognition systems to provide hands free voice control of the devices. Although voice recognition technologies have been improving, accurate voice recognition remains a technical challenge.

A particular challenge when implementing voice recognition systems on mobile devices is that, as the mobile device moves or is positioned in certain ways, the acoustic environment of the mobile device changes accordingly thereby changing the sound perceived by the mobile device's voice recognition system. Voice sound that may be recognized by the voice recognition system under one acoustic environment may be unrecognizable under certain changed conditions due to mobile device motion or positioning.

More specifically, the mobile device acoustic environment impacts the operation of signal processing components such as microphone arrays, noise suppressors, echo cancellation systems and signal conditioning that is used to improve voice recognition performance. When a mobile device is placed on or near a table or other surface, the result is a change of the transfer function between the mobile device microphones, the relative signal strength and phase of the microphone signals, and creation of additional reflections, all of which negatively impact the operation of the signal processing components, rendering them sub-optimal. For example, where a microphone array is used, changes in the acoustic environment results in undesirable changes in the array directivity, and increases pick-up of undesired sound sources.

DETAILED DESCRIPTION

Figure 1:
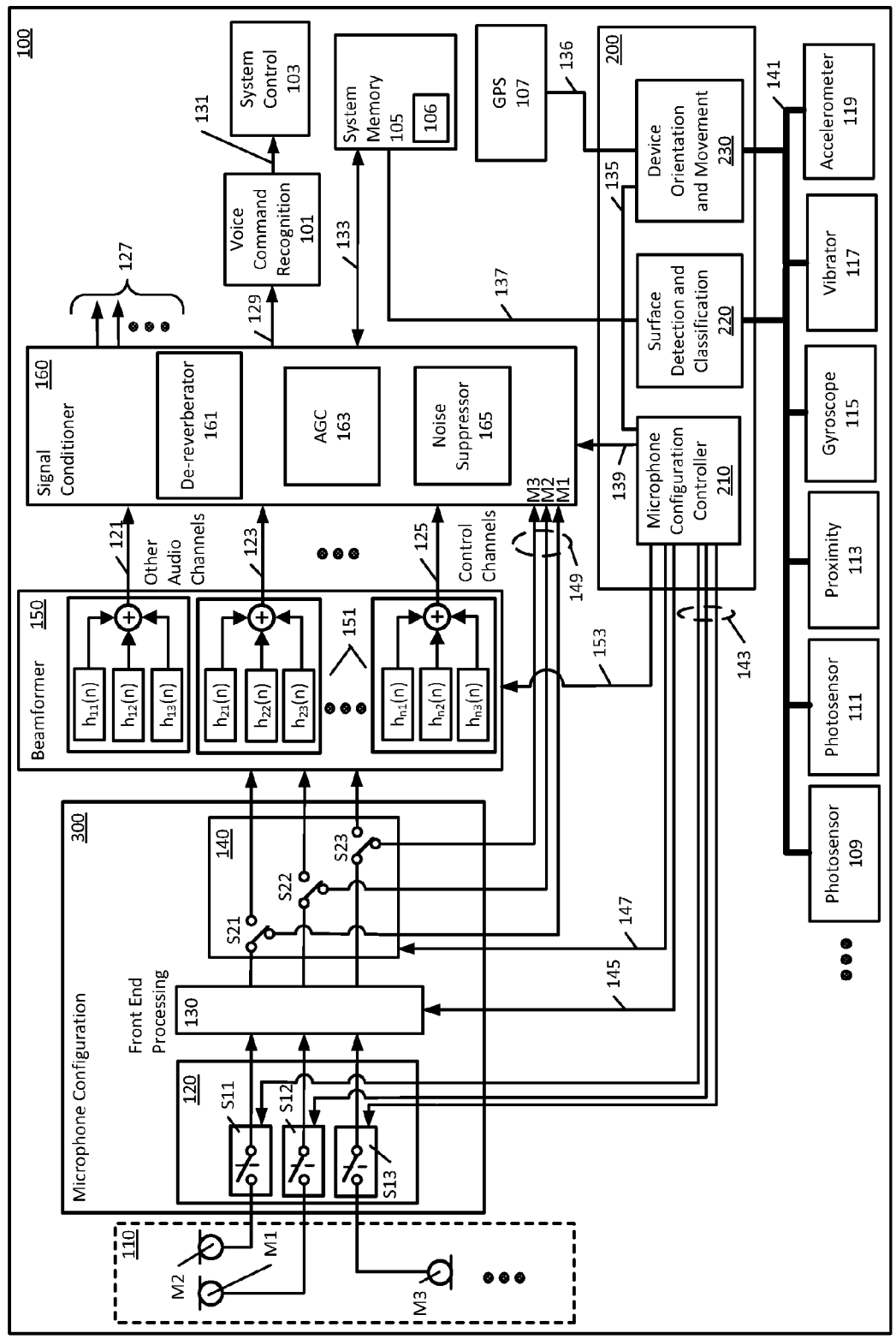
FIG. 1 is a schematic block diagram of an apparatus having a voice recognition system in accordance with the embodiments.

The present disclosure provides an apparatus and methods of operation that improve voice recognition performance of a voice recognition system in a mobile device. The voice recognition performance is improved in the various embodiments by providing adaptive adjustment of microphone configuration including switching off occluded microphones or adjustment of signal conditioning and beamforming parameters based on surface proximity to the mobile device, the type of surface in proximity, and, in some embodiments, the mobile device motion. The mobile device detects proximal surfaces with respect to the mobile device's orientation, classifies the surfaces based on surface reflectivity or absorptivity, and accordingly configures the microphones and/or adjusts the various parameters. Mobile device sensors are used to obtain a signature that may be correlated to the surface type and acoustic reflectivity or acoustic absorptivity characteristics using predetermined signatures stored in memory.

The present disclosure provides a method of operation that includes detecting a surface in proximity to a mobile device using sensor data, and determining whether the surface is acoustically reflective or acoustically absorptive. The method of operation may further include compensating for the surface acoustic reflectivity or absorptivity by controlling a configurable group of microphones of the mobile device. The present disclosure provides another method of operation that includes determining that a first microphone, of a group of microphones of a mobile device, is impeded by a surface that is in proximity to the mobile device, and turning off the first microphone. The method may include turning on a second microphone that is determined not to be impeded by the surface. The method may include detecting the surface that is in proximity to the mobile device, and using sensor data obtained from at least one sensor of the mobile device to determine acoustic reflectivity or acoustic absorptivity of the surface.

The method may further include determining orientation of the mobile device, and determining that the first microphone is impeded by the surface using the orientation and the first microphone's known position in the mobile device. The method may further include selecting signal conditioning parameters based on the acoustic reflectivity or acoustic absorptivity of the surface. Selection of signal conditioning parameters based on the acoustic reflectivity or acoustic absorptivity of the surface may be accomplished in some embodiments by selecting signal conditioning parameters from a memory table correlating a plurality of sets of signal conditioning parameters to surface types for predetermined conditions. De-reverberation may also be applied to an output of the second microphone when the surface acoustic reflectivity or acoustic absorptivity characteristic is determined to be reflective.

The method of operation may also include turning on a third microphone that is determined not to be impeded by the surface and beamforming the outputs of the second microphone and the third microphone to create a voice recognition virtual microphone.

In some embodiments, a surface that is in proximity to the mobile device may be detected by actuating a vibrator of the mobile device and obtaining data from an accelerometer of the mobile device where the data exhibits a signature of the surface's surface type.

The present disclosure provides one embodiment of an apparatus that includes a configurable group of microphones with each microphone of the group operative to be turned on or off, or have gain, attenuation or filtering applied to a corresponding microphone output in response to control signals. The apparatus also includes a signal conditioner that is operatively coupled to the configurable group of microphones and a surface compensator operatively coupled to the configurable group of microphones and to the signal conditioner. The surface compensator is operative to detect a surface in proximity to the apparatus and determine a surface acoustic reflectivity or acoustic absorptivity. The surface compensator may be further operative to control the configurable group of microphones or the signal conditioner to compensate for the surface acoustic reflectivity or acoustic absorptivity. The present disclosure also provides an apparatus in another embodiment that includes a group of microphones or microphone array, and switch logic operatively coupled to the group of microphones. The switch logic is operative to switch each microphone of the group of microphones either on or off in response to a first control signal. A signal conditioner is operatively coupled to the switch logic and to the group of microphones, and is operative to receive outputs from each microphone of the group of microphones. Voice recognition logic is operatively coupled to the signal conditioner. A surface compensator is operatively coupled to the switch logic and to the signal conditioner, and is operative to determine that a first microphone, of the group of microphones, is impeded by a surface that is in proximity to the apparatus and accordingly turn off the first microphone by sending the first control signal to the switch logic.

The apparatus may further include a plurality of sensors, operatively coupled to the surface compensator. In one embodiment, the apparatus includes a vibrator and an accelerometer, both operatively coupled to the surface compensator, where the accelerometer is one sensor of the plurality of sensors. The surface compensator is operative to detect a surface in proximity of the apparatus by actuating the vibrator and obtaining data from the accelerometer where the data exhibits a signature of the surface's surface type. The surface compensator is also operative to select signal conditioning parameters based on the signature of the surface's surface type and adjust the signal conditioner with the selected signal conditioning parameters.

In some embodiments, the apparatus includes changeover switch logic, operatively coupled to the switch logic, and a beamformer, operatively coupled to the changeover switch logic and to the signal conditioner. The beamformer is operative to receive and beamform microphone outputs from the changeover switch logic to create a virtual microphone and to provide at least one voice recognition channel from the virtual microphone to the signal conditioner. The surface compensator is operatively coupled to changeover switch logic, and is operative to send a second control signal to the changeover switch logic to control the changeover switch logic to switch each microphone of the group of microphones either to the beamformer or to the signal conditioner.

In some embodiments the apparatus includes a 3D gyroscope where the 3D gyroscope is one of the plurality of sensors. The surface compensator may determine orientation of the apparatus by obtaining 3D gyroscope data and may determine that the first microphone, of the group of microphones, is impeded by the surface based on the orientation of the apparatus and the first microphone's know position in the apparatus.

In some embodiments, the signal conditioner may include a noise suppressor and a de-reverberator. Also in some embodiments, the apparatus may include global positioning system logic, operatively coupled to the surface compensator. The surface compensator may receive global positioning system data from the global positioning system logic and determine when the apparatus is in motion in a vehicle based on the global positioning system data. The apparatus may further include non-volatile, non-transitory memory, operatively coupled to the surface compensator. The surface compensator may access the memory to compare the observed signature of the surface's surface type to a table of stored predetermined signatures and select the signal condition parameters from the table based on a matching predetermined signature.

Turning now to the drawings, FIG. 1 illustrates a schematic block diagram of a mobile device 100, which is an example apparatus in accordance with the embodiments. The mobile device 100 is an example apparatus that has the features and advantages of, among other things, a surface compensator 200. It is to be understood that FIG. 1 is limited to showing only those components useful to describe the features and advantages of the various embodiments, and to describe how to make and use the various embodiments to those of ordinary skill. It is therefore to be understood that various other components, circuitry, and devices etc. may be present in order to implement an apparatus such as mobile device 100 and that those various other components, circuitry, devices, etc., are understood to be present by those of ordinary skill. For example, the mobile device 100 may include inputs for receiving power from a power source, a power distribution bus, a battery, communication buses for sending control signals or other information between operatively coupled components, etc. Thus it is to be understood that such various other components, circuitry, or devices are omitted for the purpose of clarity.

The various components, circuitry, devices etc. described with respect to the figures including, but not limited to, those described using the term "logic," may be implemented in various ways such as by software and/or firmware executing on one or more programmable processors such as a central processing unit (CPU) or the like, or by ASICs, DSPs, FPGAs, hardwired circuitry (logic circuitry), or any combinations thereof.

The terminology "operatively coupled" as used herein refers to coupling that enables operational and/or functional communication and relationships between the various components, circuitry, devices etc. described as being operatively coupled and may include any intervening items (i.e. buses, connectors, other components, circuitry, devices etc.) used to enable such communication such as, for example, data communication buses or any other intervening items that one of ordinary skill would understand to be present. Also, it is to be understood that other intervening items may be present between "operatively coupled" items even though such other intervening items are not necessary to the functional communication facilitated by the operative coupling. For example, a data communication bus may be present in various embodiments and may provide data to several items along a pathway along which two or more items are operatively coupled, etc. Such operative coupling is shown generally in FIG. 1 described herein.

In FIG. 1 the mobile device 100 is an example apparatus in accordance with the embodiments and includes a voice recognition system. The mobile device 100 may be any of various mobile devices such as, but not limited to, a video camera, smartphone, tablet computer, laptop, audio recorder, or some other electronic device, etc. In the mobile device 100, a group of microphones 110 provide microphone outputs that are operatively coupled to microphone configuration logic 300. In some embodiments, the microphone configuration logic 300 may include switch logic 120, front end processing 130 and changeover switch logic 140. The microphone configuration logic 300 together with the group of microphones 110 forms a configurable group of microphones that may be each individually turned on or off, or have gain, attenuation or filtering applied to a corresponding microphone by the front end processing 130. In other words, the microphone configuration logic 300 is controllable by appropriate control signals. Although the example of FIG. 1 shows three microphones, the embodiments are not limited to three microphones and any number of microphones may be used in the embodiments. Each microphone M1, M2 and M3 of the group of microphones 110, is operatively coupled to a corresponding switch S11, S12 and S13 of switch logic 120. The switches S11, S12 and S13 are operative to turn their respective microphones on or off in response to a control signal received from a surface compensator 200. That is, the switches S11, S12 and S13 operate as single pole, single throw (SPST) on-off switches. The switches may be implemented in any suitable manner such as by tri-state logic (i.e. a tri-state buffer as an SPST switch, etc.) or some other implementation as understood by those of ordinary skill.

The surface compensator 200 is operatively coupled to the switch logic 120 by, for example, an internal communication bus of the mobile device 100. The surface compensator 200 provides control signals 143 to the switch logic 120 and may turn any one of the microphones M1, M2 and M3 on or off in any combination by sending the appropriate control signal 143 to the appropriate switch S11, S12 or S13, respectively.

The outputs of switch logic 120 are operatively coupled to front end processing 130, which may include, but is not limited to, signal amplification, analog-to-digital conversion/digital audio sampling, echo cancellation, etc., which may be applied to the physical microphone M1, M2, M3 outputs prior to the beamformer 150 or signal conditioner 160. In some embodiments, the front end processing 130 may receive a control signal 145 from the surface compensator 200 to adjust parameters such as, for example, amplifier gain.

The front end processing 130 is further operatively coupled to changeover switch logic 140. Changeover switch logic 140 is operatively coupled to the surface compensator to receive control signal 147, and includes a switch operatively coupled and corresponding to each microphone output, for example switches S21, S22 and S23. The switches S21, S22 and S23 are configured as a single-pole, double throw (SPDT) changeover switches in that each switch is operative to switch its respective microphone output to the beamformer 150 or directly to the signal conditioner 160. In other words, the changeover switch logic 140 is controlled by the surface compensator 200 to turn beamforming on or off. In other embodiments, the beamformer 150 may be turned on or off by control signal 153 from the microphone configuration controller 210. Microphones may be effectively turned on or off by the beamformer 150 by increasing gain on microphone inputs to turn microphones on and by adjusting gain to zero to turn microphones off That is, in some embodiments the beamformer bypass operation of the changeover switch logic 140 may be performed by the beamformer 150 and the changeover switch logic 140 and/or switch logic 120 may not be used or may not be present in the embodiment. Instead, in some embodiments, the microphone configuration controller 210 may control the beamformer 150 by control signal 153 to implement the operations of the microphone configuration logic 300 switches.

The beamformer 150 is an adjustable beamformer and receives audio signals from the microphone M1, M2 and M3 outputs and performs beamforming to create various virtual microphone audio channels that include at least one voice recognition control channel 125. In some embodiments, the beamformer 150 may provide other virtual microphone audio channels such as audio channels 121 and 123, which may be, for example, virtual microphone voice communication channels on a mobile phone, virtual microphone voice recording channels on a video recorder, or some other type of virtual microphone audio channel. In other embodiments, multiple voice recognition channels may be created by beamformer 150 in addition to voice recognition control channel 125.

The beamformer 150 creates the virtual audio channels by applying appropriate filtering algorithms and using a group of adjustable filters 151 which, in some embodiments, may be adaptive filters. In one example, sound received by microphones M1, M2 and M3 may be combined and appropriately filtered to create a single "virtual microphone" that receives sound from a given direction. As mentioned above, the group of microphones 110 may include several microphones (i.e. a microphone array) such that one or more virtual microphones may be created using several physical microphone outputs and applying beamforming techniques. As a few examples, the created virtual microphones may be used to focus on sound in any given direction or to pan a room to search for specific voices, sounds, etc. Therefore, the beamformer 150 may be used to create one or more virtual microphones to pick up sound coming from the direction of the controlling user while another virtual microphone may pick up sound in a direction where another speaker is located such as, for example, in a conference call situation where two speakers are located in different areas of a room.

The example beamformer 150 includes various filters such as filter 151 which provide the various other audio channels 121 and 123 and the voice recognition control channel 125. As shown in FIG. 1, the beamformer 150 may have any number of filters. Likewise, the number of virtual audio channel outputs is not limited. The filters 151 may be finite impulse response (FIR) filters in some embodiments and may also be adaptive FIR filters. Additionally, in some embodiments, outputs from one or more filters may be combined, or summed, to create a virtual audio channel. That is, in accordance with the embodiments, any appropriate filter configuration may be implemented within the beamformer 150.

The beamformer 150 is operatively coupled to a signal conditioner 160 and provides the virtual microphone audio channels as inputs. It is to be understood however that the signal conditioner 160 could also be located prior to the beamformer 150 and therefore may be operatively coupled to the microphone outputs at changeover switch logic 140 or elsewhere such that the signal conditioner 160 may provide conditioned microphone outputs to the beamformer 150 in some embodiments. In the example embodiment of FIG. 1, the various audio channels 121 and 123, and voice recognition control channel 125 are input to the signal conditioner 160. The signal conditioner 160 is also operatively coupled to changeover switch logic 140, and may receive microphone inputs 149 directly when the changeover switch logic 140 is switched to bypass the beamformer 150. The signal conditioner 160 is also operatively coupled to the voice command recognition logic 101 to provide a conditioned control channel 129 as an input to the voice command recognition logic 101. The voice command recognition logic 101 is operatively coupled to the system control 103, which may be any type of voice controllable system control such as, but not limited to, a voice controlled dialer of a mobile phone, a video system control, an application control of a mobile phone, smartphone, tablet, laptop, etc., or any other type of voice controllable system control. The voice command recognition logic 101 send a control signal 131 to the system control 103 in response to detected command words or command phrases received on the conditioned voice recognition control channel 129. The signal conditioner 160 may provide a conditioned output, corresponding to each signal conditioner 160 input. For example, signal conditioner 160 may provide conditioned audio channels 127 to some other mobile device 100 system such as a transceiver. The transceiver may be a wireless transceiver using any of various wireless technologies and may implement a full duplex telecommunication channel. The conditioned voice recognition control channel 129 is input to the voice command recognition logic 101 as note above.

The surface compensator 200 is operatively coupled to the signal conditioner 160 to provide a control signal 139. The surface compensator 200 may send the control signal 139 when the surface compensator 200 detects a reflective or absorptive surface in proximity to the mobile device 100. In response to detection of a surface, and determination of a surface type, the surface compensator 200 may send the control signal 139 to the signal conditioner 160 and may control any of various audio attributes related to various audio enhancement functions in order to compensate for the proximate surface. The signal conditioner 160 may include various audio enhancement functions such as, but not limited to, de-reverberator 161, automatic gain control (AGC) 163, or noise suppressor 165, etc.

The surface compensator 200 is also operatively coupled to the beamformer 150 to provide a control signal 153, which may also be sent in response to detection of a surface, and determination of a surface type. For example, the control signal 153 may control attributes of the filters 151 to change the configuration of virtual microphones or redirect the virtual microphone beams, etc., or to adjust some other audio attribute. By controlling the filters 151, the beamformer 150 may beamform the sound received by each of the microphones M1, M2 and M3, in any combination, to create virtual microphones and particularly voice recognition control channel 125. That is, in accordance with the embodiments, sound received by various physical microphones may be combined in various ways to form virtual microphones that may be reconfigured in response to a microphone impeding surface detected by the surface compensator 200.

For example, the surface compensator 200 may configure virtual microphones to compensate for an impeding proximal surface by focusing on a given direction, amplifying a specific voice or sound, panning, or etc. The surface compensator 200 may include a microphone configuration controller 210 that is operative to compensate for surfaces impeding any one or more microphones of the group of microphones 110 by turning microphones on or off and by controlling audio attributes such as, but not limited to, audio sensitivity, panning in a given direction, focusing on a specified direction, blocking a specified direction, or reducing background noise, etc.

The voice recognition control channel 125 may be created using beamforming where the virtual microphone is configured to pick up sound from a certain position with respect to the mobile device 100. More particularly, a virtual microphone may be created that is directed towards the operator of mobile device 100 and that avoids an impeding surface that impedes one or more physical microphones of the mobile device 100. Command word utterances are detected on the voice recognition control channel 125 by the voice command recognition logic 101 and acted upon appropriately.

In one example embodiment, the microphone configuration controller 210 of the surface compensator 200 controls the beamformer 150 among other things. The example microphone configuration controller 210 may include an internal memory table, or may access a memory table 106 stored in system memory 105, which is operatively coupled to the surface compensator 200 by connection 137. The memory table 106 may store preconfigured beam patterns for predetermined virtual microphone configurations. The preconfigured beam patterns may be stored by storing filter coefficients or other filter parameters that may be used by the beamformer 150 and applied to the group of filters 151 to create the desired audio beam patterns. The microphone configuration controller 210 is operatively coupled to the beamformer 150 to send a control signal 153 to adjust the beamformer 150 settings. The control signal 153 may include settings obtained from the memory table 106 or may provide a pointer to a memory table 106 location that may be accessed by the beamformer 150 to adjust settings.

The system memory 105 is a non-volatile, non-transitory memory, and may be operatively coupled to the signal conditioner by connection 133 and may also be accessible by other components of the mobile device 100 for various setting, stored applications, etc. In embodiments where the system memory 105 is used to store the memory table 106, the surface compensator 200 is operatively coupled to the system memory 105 to send data to, and receive data from, the system memory 105 over connection 137 which is a bi-directional memory interface.

The microphone configuration controller 210 of the surface compensator 200 may also control the signal conditioner 160 by using the memory table 106. That is, the memory table 106 may store various audio parameters for predetermined audio attributes. The stored audio parameters may include noise suppression algorithms that may be selected for a noise suppression component of signal conditioner 160 or some other audio related algorithms to achieve the desired audio attributes to overcome voice recognition issues due to motion or an impeding surface.

It is to be understood that the various "control signals" described herein with respect to various components such as, but not limited to, the surface compensator 200, switch logic 120, changeover switch logic 140, front end processing 130, beamformer 150, signal conditioner 160, etc., may be implemented in various ways such as using APIs between the various components. Additionally, operations involving the memory table 106 may be implemented using pointers where the components access the memory table 106 as directed by the microphone configuration controller 210. In other words, control signal 153 and control signal 139 may be implemented such that the beamformer 150 and the signal conditioner 160 obtain control information such as, but not limited to, audio attribute parameters, filter coefficients etc., from system memory 105 and that such implementations are contemplated embodiments and in accordance with the embodiments and examples described herein.

The surface compensator 200 may include surface detection and classification logic 220 and device orientation and movement logic 230, both of which are operatively coupled to each other and to the microphone configuration controller 210 by communication bus 135 which may be internal to the surface compensator 200. The communication bus 135 may be implemented as application programming interfaces (APIs) between the surface compensator 200 components in some embodiments. The mobile device 100 includes a group of sensors that are all operatively coupled to the surface compensator 200 by a communication bus 141. The group of sensors may include, but is not limited to, photosensor 109, photosensor 111 (such as cameras), proximity sensor 113, 3D gyroscope 115, vibrator 117 and accelerometer 119. The surface compensator 200 may also be operatively coupled to global positioning system (GPS) logic 107 by connection 136, to receive location data and speed information when the mobile device 100 is in motion such as when it is located in a vehicle.

In accordance with the embodiments, the surface compensator 200 uses the group of sensors to detect a surface such as when a mobile device is placed on a table. The surface compensator 200 is operative to enable one or more microphones of the group of microphones 110 as appropriate to avoid the impeding surface. The surface compensator 200 may also use mobile device 100 orientation to select an appropriate microphone. For example, microphones M1 and M2 may be located at top and bottom edges of a front side the mobile device 100 and microphone M3 may be located somewhere on a rear side of the mobile device 100. The device orientation and movement logic 230 of surface compensator 200 uses data from accelerometer 119 or GPS logic 107 to determine if the mobile device 107 is moving or is stationary such as when the mobile device 100 is on a table top. More particularly, the device orientation and movement logic 230 may use the accelerometer 119 or gyroscope 115 to determine the orientation of the mobile device 100. For example, if the mobile device 100 is not determined to be moving and is in an orientation relatively perpendicular (with respect to the ground), the device orientation and movement logic 230 may determine that the mobile device 100 is stationary and may have been placed on a surface.

If the device is determined to have been placed on or near a surface, the device orientation and movement logic 230 may send a trigger to the surface detection and classification logic 220 to check for surfaces. However, in other embodiments, the surface detection and classification logic 220 may independently perform checks for nearby surfaces by obtaining data from the group of sensors. For example, photosensor 109, photosensor 111 or proximity sensor 113 may provide an indication to surface detection and classification logic 220 of a nearby surface. The surface detection and classification logic 220 actuates the vibrator 117 and performs a closed-loop measurement by obtaining feedback from the accelerometer 119 or the gyroscope 115 or both. The information obtained is used to determine if a surface is present, such as when the mobile device 100 is placed on a table, chair cushion, car seat, next to a wall, etc., and to determine a surface classification such as whether the surface is reflective or absorptive. The orientation of the mobile device 100 may be used by the surface compensator 200 in conjunction with the surface classification information to determine how to configure the microphones to compensate for the surface's acoustic reflectivity or acoustic absorptivity.

For example, the device orientation and movement logic 230 will inform the microphone configuration controller 210 of the mobile device 100 orientation, and the surface detection and classification logic 220 will provide the surface type (i.e. surface classification; reflective, absorptive, etc.). One or more microphones may be impeded by a surface due to surface reflectivity or surface absorptivity (i.e. occlusion) based on the surface type and the mobile device orientation with respect to the surface. For example, if the mobile device is found to be oriented such that microphone M3 is facing downward, the microphone configuration controller can open switch S13 to turn off microphone M3 since it may be impeded by a surface. Alternatively, the microphone configuration controller 210 may send control signal 153 to beamformer 150 and apply beamforming to one or more of the microphone outputs to avoid interference from the surface. Other beamforming configurations may be used when the mobile device 100 is determined to be, or is most likely to be, in the user's hand. The microphone configuration controller 210 will also control the signal conditioner 160 to adjust various audio attributes. For example, if a surface is found to be reflective, the microphone configuration controller 210 may send control signal 139 to the signal conditioner 160 to invoke the de-reverberator 161. Thus the surface compensator 200, among other features, detects a surface in proximity to the mobile device 100 and determines an acoustic reflectivity or acoustic absorptivity of the surface by using sensor data obtained from the group of sensors operatively coupled by communication bus 141. The surface compensator 200 compensates for the surface acoustic reflectivity or acoustic absorptivity by controlling the configurable group of microphones, controlling the signal conditioner 160, controlling the beamformer 150, or by combinations of each of these. Compensating for the proximate surface by the surface compensator 200 may include, among other things, inferring a time delay via the speed of sound and/or estimating the relative strength of the initial acoustic reflection from that surface via estimates of the surface reflectivity or absorptivity. This information may be used in some embodiments to configure the parameters of beamformer 150 or of signal conditioner 160 modules such as the de-reverberator 161. Additionally, such information along with the known 3D locations of the microphones can be used by the microphone configuration controller 210 and beamformer 150 to determine a useful orientation for a virtual microphone and configure the beamform pattern accordingly. In some embodiments, compensating for the proximate surface may also include using beamforming to avoid acoustic inference by the surface (i.e. reflected sound waves or sound absorption) or by adjusting signal conditioning such as de-reverberation, gain, etc. to accommodate for reflections or for signal attenuation due to absorption.

Various methods of operation of the surface compensator 200 may be understood in view of the flowcharts of FIG. 2 through FIG. 6. Beginning with FIG. 2, a method of operation begins in operation block 201 in which the surface compensator 200 determines the motion status of the mobile device 100. In operation block 203 the surface compensator 200 determines the orientation of the mobile device 100 such as, for example, whether the mobile device 100 is oriented perpendicular to the ground or horizontal with respect to the ground such as when it is placed upon a flat surface such as a tabletop or chair cushion, etc. In operation block 205, the surface compensator 200 determines if the mobile device 100 actually is located on or near a surface. If the mobile device 100 is actually located on or near a surface, the surface compensator 200 will determine the surface type in operation block 207. The surface type is a surface classification, such as whether the surface is reflective or absorptive, which may be determined by a sensor data signature obtained by the surface compensator 200. In operation block 207, the surface compensator 200 will configure the group of microphones 110 and will apply appropriate signal conditioning, which may include beamforming, according to the determined motion status, orientation, and surface type. The method of operation then ends as shown.

Figure 2:
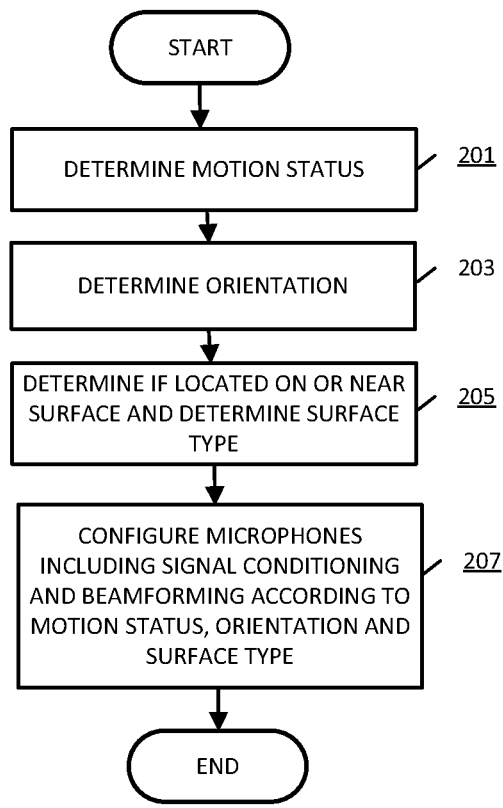
FIG. 2 is a flow chart showing a method of operation of an apparatus with a surface compensator in accordance with various embodiments.
Figure 3:
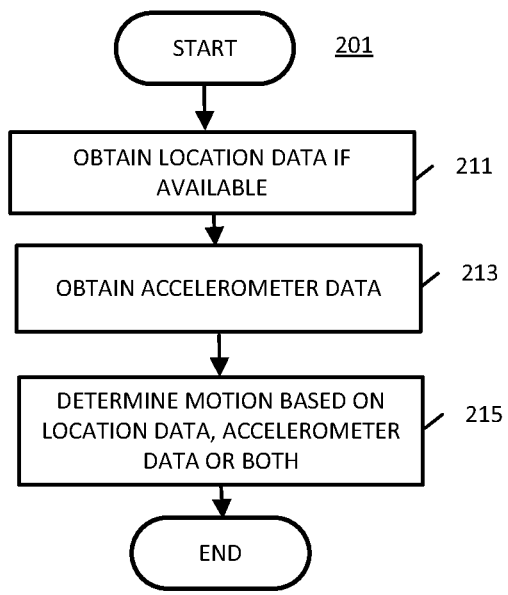
FIG. 3 is a flow chart providing details of one operation of the method shown in FIG. 2, in accordance with an embodiment.

The flowchart of FIG. 3 provides details of a method of operation that occurs within operation block 201 of FIG. 2. That is, in some embodiments as shown in operation block 211, the surface compensator 200 may obtain location data such as, but not limited to, GPS data from GPS logic 107. The GPS data is processed by the surface compensator 200 to determine the location of the mobile device 100 and if the mobile device 100 is in a moving vehicle. In some situations, GPS data may not be available such as when the mobile device 100 is unable to access the GPS signal. In those situations, as shown in operation block 213, surface compensator 200 may obtain accelerometer data from the accelerometer 119. In operation block 215, the surface compensator 200 may determine motion status of mobile device 100 based on the obtained location data if it was available, accelerometer data, or both. The motion status determination is made by the device orientation and movement logic 230 of the surface compensator 200. The method of operation in the flow chart of FIG. 3 then ends and, in the flowchart of FIG. 2, the method of operation proceeds to determine the mobile device 100 orientation as shown in operation block 203. Returning briefly to operation block 203 of FIG. 2, the device orientation and movement logic 230 may assess data obtained from the 3D gyroscope 115 to determine if the mobile device 100 is oriented horizontally or at some acute angle with respect to the ground such that it may be positioned on or near a surface.

Figure 4:
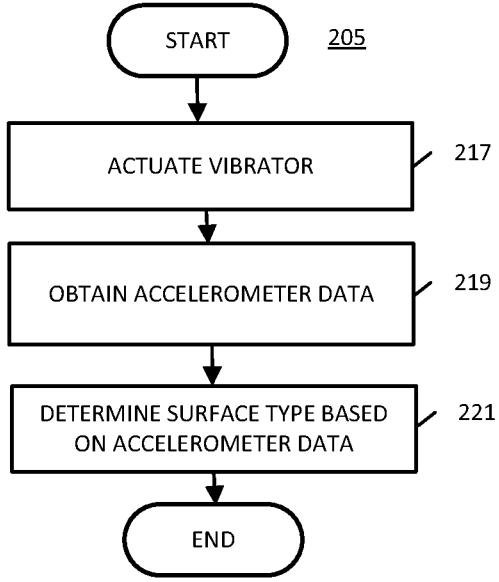
FIG. 4 is a flow chart providing details of another operation of the method shown in FIG. 2 in accordance with an embodiment.

If a determination is made by the device orientation and movement logic 230 that mobile device 100 is not in a moving vehicle, information from any combination of the group of sensors may be combined to determine the mobile device 100 orientation and whether the mobile device 100 may be near a surface. The device orientation and movement logic 230 provides an output, over the communication bus 135, to the surface detection and classification logic 220 which includes the mobile device 100 orientation, and a flag indicating that the mobile device 100 may be on, or close to, a surface. In response to the control signal, the surface detection and classification logic 220 proceeds with the method of operation shown in FIG. 4, which also occurs in operation block 205 of FIG. 2. Therefore, FIG. 4 provides further details of operation block 205. Thus, in FIG. 4 operation block 217, the surface detection and classification logic 220 activates vibrator 117 while monitoring the accelerometer 119 signal. That is, the accelerometer data is obtained as shown in operation block 219. The accelerometer 119 signal is then analyzed for characteristics such as frequency distribution, level, etc. and is compared to known predetermined signatures that are stored in system memory 105. These signatures may be stored in the memory table 106. In operation block 221, the known signatures based on the accelerometer data are used to determine the surface type. The method of operation of FIG. 4 then ends and the surface detection and classification logic 220 then provides an output, over the communication bus 135, to the microphone configuration controller 210. The method of operation proceeds to operation block 207 in FIG. 2, further details of which are provided in FIG. 5.

Therefore the microphone configuration controller 210 receives information from the surface detection and classification logic 220 regarding the surface type. The microphone configuration controller 210 may also receive orientation information from the device orientation and movement logic 230. The microphone configuration controller 210 then uses the received information to configure a microphone array unit such as the group of microphones 110, and determines which microphones to be activated or turned off, the microphone gains at front end processing 130, beamforming and signal conditioning based on a set of rules which may be stored in system memory 105. The rules are predetermined based on various surface types and signatures and orientations of the mobile device 100 with respect to such surface types. The microphone configuration controller 210 may therefore control the beamformer 150 to form optimal virtual microphones for a given surface type and also sends control signal 139 to the signal conditioner 160 to configure the noise suppressor 165, and also the AGC 163 and de-reverberator 161 when needed.

Figure 5:
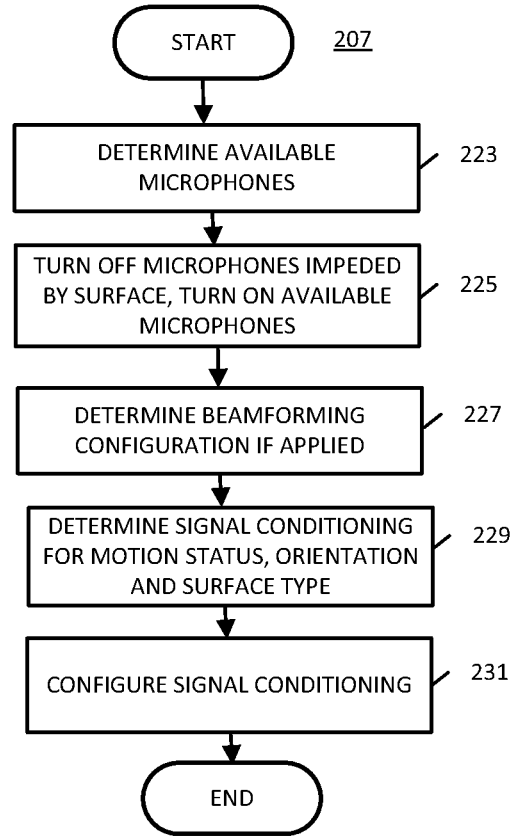
FIG. 5 is a flow chart providing details of another operation of the method shown in FIG. 2 in accordance with an embodiment.

These operations of the microphone configuration controller 210 occur in operation block 207 of FIG. 2, further details of which are provided by the flowchart of FIG. 5. Thus, in FIG. 5 operation block 223, the microphone configuration controller 210 determines which microphones of the group of microphones 110 are available. For example, some microphones may be occluded or impeded by an absorptive surface, such as a couch cushion. Additionally, in some embodiments, some microphones may be unavailable for voice recognition if they are being used by the mobile device 100 for other audio activities, for example, audio recording, voice communication, etc. However, such "in use" microphones may be used in some embodiments to form a virtual microphone and virtual voice recognition channel using beamforming. Thus in operation block 225, the microphone configuration controller 210 may turn some microphones on and others off accordingly. In operation block 227, the microphone configuration controller 210 will determine whether beamforming should be applied and will send control signal 153 to beamformer 150 to adjust parameters accordingly if applicable. That is, the microphone configuration controller 210 may operate changeover switch logic 140 to turn beamforming on or off accordingly for one or more activated microphones, and configure the beamformer 150 by control signal 153. In operation block 229, the microphone configuration controller 210 will also determine what signal conditioning should be applied given the mobile device 100 motion status, orientation and surface type of any nearby surface. This determination may be made by performing a lookup operation of signal conditioning configurations for known conditions stored in system memory 105. In operation block 231, the microphone configuration controller 210 sends control signal 139 to the signal conditioner 160 to configure signal conditioning accordingly. The method of operation of FIG. 5, and also of FIG. 2, then ends.

Returning briefly to operation block 201 and the flowchart of FIG. 3, if a determination is made that the mobile device 100 is inside a moving vehicle, orientation and surface detection is attempted after accounting for the variability in the accelerometer 119 and 3D gyroscope 115 signals. The presence and characteristics of a surface is tested by the surface detection and classification logic 220. The statistic of the information obtained, and criteria such as signal distribution, (variance, or other statistical measures) are used to determine if the attempted surface detection was successful or not. Upon a determination that the decision is un-reliable, a "default in-car configuration" signal is sent to the microphone configuration controller 210, otherwise the microphones are configured accordingly for a detected surface as described above.

Figure 6:
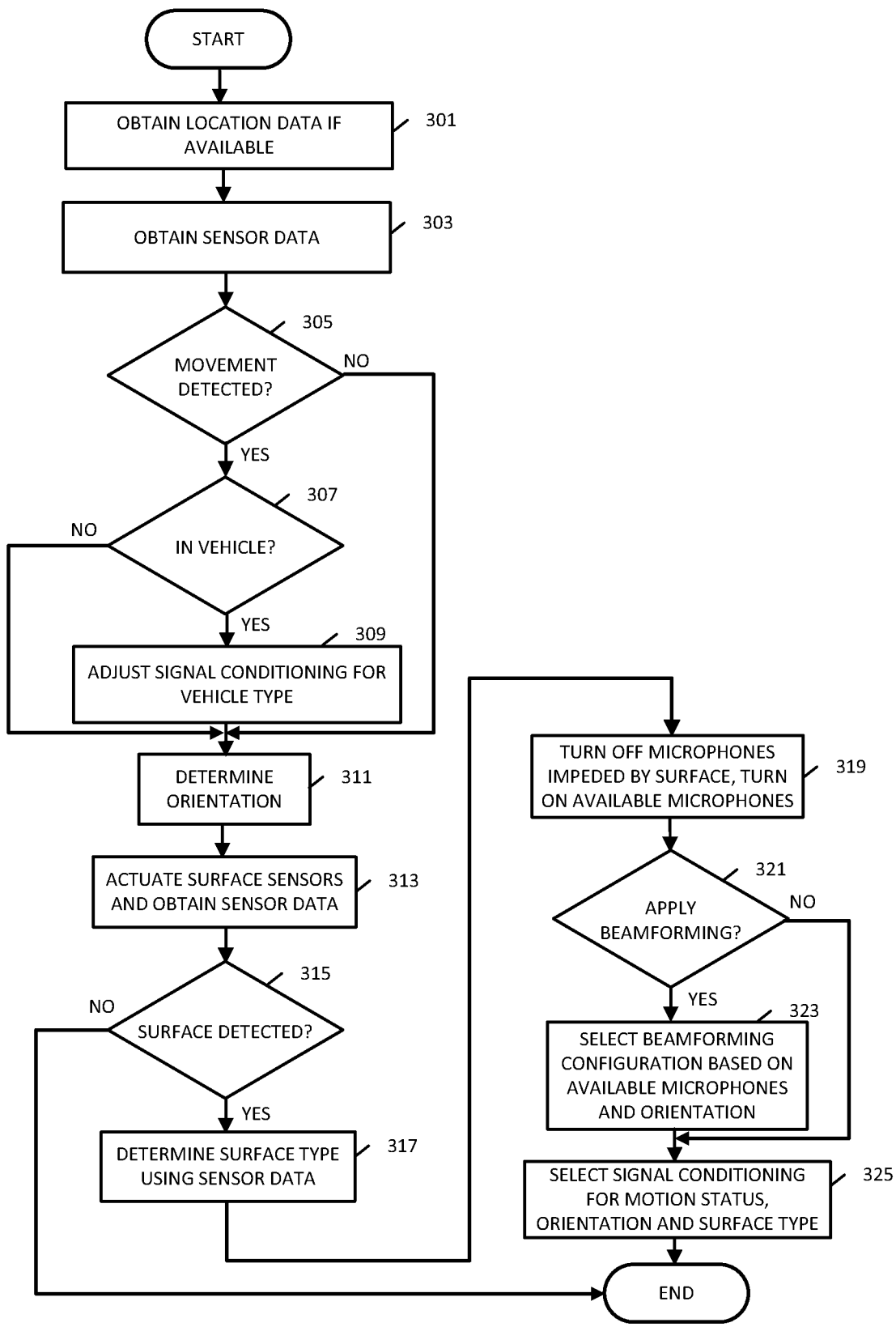
FIG. 6 is a flow chart showing a method of operation of an apparatus with a surface compensator in accordance with various embodiments.

The flowchart of FIG. 6 is useful for understanding an overall method of operation of the surface compensator 200. The method of operation begins in operation block 301, and the surface compensator 200 obtains location data from the GPS logic 107 if location data is available. In operation block 303, the surface compensator 200 obtains sensor data from any or all of the sensors such as, but not limited to, photosensor 109, photosensor 111, proximity sensor 113, 3D gyroscope 115, and accelerometer 119. In decision block 305, the surface compensator 200 checks the obtained location data, as well as gyroscope 115 and accelerometer 119 data, to determine if the mobile device 100 is moving. If no movement is detected in decision block 305, then the method of operation proceeds to determine orientation of the mobile device 100 in operation block 311.

However, if movement is detected in decision block 305, then the surface compensator 200 will proceed to decision block 307 and will determine if the mobile device 100 movement is caused by the mobile device 100 being located in a vehicle. If not, then the method of operation again proceeds to operation block 311 to determine the mobile device 100 orientation. However, if the mobile device 100 is determined to be in a vehicle in decision block 307, then the surface compensator 200 may adjust signal conditioning for the vehicle type in operation block 309. The surface compensator 200 may obtain settings for the signal conditioner 160 from system memory 105 based on known sensor data signatures, that are known for in-vehicle acoustic conditions for a given vehicle type, and may select settings that match the observed sensor signatures obtained in operation block 303.

In operation block 311, the surface compensator 200 determines the orientation of the mobile device 100 by reading the sensor data obtained from 3D gyroscope 115. The orientation may indicate that there is a likelihood that the mobile device 100 is placed on or near a surface, such as, for example, when the mobile device 100 is laid on the table or some other relatively flat surface. In response to such a determination, as shown in operation block 313, the surface compensator 200 may proceed to actuate surface sensors and obtain sensor data to attempt to detect a nearby surface. For example, the surface compensator 200 may actuate vibrator 117 of mobile device 100 and monitor the response of accelerometer 119 to determine a surface signature and thus to determine whether a surface is present. If a surface is detected in decision block 315 then, in operation block 317, the surface compensator 200 may determine the surface type using the sensor data. For example, surface compensator 200 may access the memory table 106 stored in system memory 105, to compare a measured signature to predetermined signatures that have been previously measured for known surface types and for given mobile device orientations. If no surface is detected in decision block 315, method of operation ends as shown.

After detection of the surface in decision block 315, and determination of surface type in operation block 317, the surface compensator 200 may turn off microphones impeded by the detected surface and turn on any available microphones as shown in operation block 319. In decision block 321, surface compensator 200 may determine whether to apply beamforming given the orientation of the mobile device 100 and the detected surface type. If the surface compensator 200 determines that beamforming should not be applied in decision block 321, then the surface compensator 200 may proceed to select signal conditioning for the motion status, orientation and surface type as shown in operation block 325, after which the method of operation ends as shown. If beamforming is to be applied in decision block 321, then the surface compensator 200 may select a beamforming configuration based on the available microphones and mobile device 100 orientation as shown in operation block 323. For example, the surface compensator 200 may access the memory table 106 or other memory tables stored in system memory 105 and obtain a beamforming configuration based on the detected surface type and mobile device 100 orientation. An appropriate beamforming configuration may be selected from a set of predetermined, stored beamforming configurations. If beamforming is not to be applied in decision block 321, or if a beamforming configuration selection is completed in operation block 323, then the surface compensator 200 proceeds to operation block 325 and selects signal conditioning parameters appropriate for the motion status, orientation and surface type. The surface compensator 200 may also access system memory 105 to obtain signal conditioning configurations that are stored for predetermined known orientations of the mobile device and know surface types. The surface compensator 200 then sends appropriate control signal 153 to the beam former 151 if beamforming is applied, and sends control signal 139 to signal conditioner 160 to accordingly adjust various parameters of the beamformer 150 and signal conditioner 160, respectively.

Therefore, among other advantages of the various embodiments, microphone configuration including application of beamforming and signal conditioning is adjusted by the surface compensator 200 to improve voice recognition performance when a mobile device 100 is placed on, or near, an audio impeding surface whether reflective or absorptive. The surface compensator 200 determines, among other things, which microphones that are not impeded or occluded for a detected mobile device 100 orientation. The surface compensator 200 may utilize a single microphone and may apply noise reduction algorithms suitable for the single microphone. The surface compensator 200 may apply a table-top optimized noise reduction algorithm and/or a table-top optimized beamforming configuration where pre-configuration information is stored in, and retrieved from, the memory table 106. The surface compensator 200 may also apply appropriately trained de-reverberation. The surface compensator 200 may use information from the proximity sensor 113 or from any of the group of sensors in various combinations to determine and select an optimal configuration for a microphone array such as the group of microphones 110 in response to detection of a nearby surface which changes the mobile device 100 acoustic environment conditions.

Among other advantages, the embodiments also provide methods for determining the characteristics of the surface (such as when a mobile device is lying on a hard surface, or on a soft cushion such as couch or car seat). In order to accomplish this task, a signal from the 3D accelerometer 119 is examined by the surface compensator 200 both with and without external stimulus from the vibrator 117. Predetermined characteristics of the signal may be stored in a database of signatures obtained in different environments and stored in system memory 105. For example, the database of signatures may be stored in memory table 106 in some embodiments.

Another advantage of the embodiments is that actions are taken in order to improve the signal sent to the voice command recognition logic 101, once accurate determination is made as to the presence of interfering surfaces near-by the group of microphones 110. These actions fall into two categories; selecting which out of many available microphones are activated, and how the signals from multiple microphones are combined for further processing.

For example, in some situations, such as where the mobile device 100 is determined by the surface compensator 200 to be laying upside-down on a soft cushion, the surface compensator 200 may further determine that a primary microphone is occluded and can accordingly switch on a secondary microphone only (for example, a microphone located on the back of the mobile device may be a "secondary" microphone)

and configure the signal conditioner 160 to apply noise reduction for a single-microphone system. If multiple microphones are available, the appropriate set of microphones can be identified by the surface compensator 200 and activated. The surface compensator 200 may then further apply beamforming and signal conditioning configured appropriately for the surface type and conditions.

Another advantage is that the presence of a very reflective surface can be mitigated by configuring the use of appropriate microphones and turning on a de-reverberation processing, prior to noise reduction. The type of algorithm may be selected based on the severity of the condition, or based on which microphone or microphones are active for the condition observed. In situations, where accurate determination about the environment condition cannot be made, a safe default microphone configuration is used.

While various embodiments have been illustrated and described, it is to be understood that the invention is not so limited. Numerous modifications, changes, variations, substitutions and equivalents will occur to those skilled in the art without departing from the scope of the present invention as defined by the appended claims.

What is claimed is:

1. A method in a mobile device having multiple microphones and a processor, the method comprising:
    determining by the processor that a first microphone, of the multiple microphones is impeded by a surface that is in contact with the mobile device;
    turning off, by the processor, the first microphone; and
    detecting the surface that is in contact with the mobile device by:
        actuating a vibrator of the mobile device; and
        responsive to actuating the vibrator, obtaining data from an accelerometer of the mobile device, the obtained data exhibiting a signature of the surface's surface type.

2. The method of claim 1, further comprising, responsive to turning off the first microphone, turning on, by the processor, a second microphone that is determined not to be impeded by the surface.

3. The method of claim 2, further comprising:
    obtaining sensor data from at least one sensor of the mobile device; and
    determining, by the processor, acoustic reflectivity or acoustic absorptivity of the surface using the obtained sensor data from the at least one sensor of the mobile device.

4. The method of claim 1, further comprising:
    determining, by the processor, the orientation of the mobile device, wherein said turning off the first microphone is performed in response to determining by the processor that the first microphone is impeded by the surface using the orientation and the first microphone's known position in the mobile device.

5. The method of claim 3, wherein determining the acoustic reflectivity or acoustic absorptivity of the surface causes the processor to select signal conditioning parameters based on the determined acoustic reflectivity or acoustic absorptivity of the surface.

6. The method of claim 5, wherein selecting signal conditioning parameters based on the acoustic reflectivity or acoustic absorptivity of the surface, comprises:
    selecting, by the processor signal conditioning parameters from a memory table correlating a plurality of sets of signal conditioning parameters to surface types for predetermined conditions.

7. The method of claim 3, wherein determining that the surface is acoustically reflective causes the processor to apply de-reverberation to an output of the second microphone.

8. The method of claim 3, further comprising:
    turning on a third microphone that is determined not to be impeded by the surface in response to turning off the first microphone; and
    creating a virtual recognition microphone by beamforming outputs of the second microphone and the third microphone.

9. An apparatus comprising:
    a group of microphones;
    switch logic, operatively coupled to the group of microphones, operative to selectively switch each microphone of the group of microphones either on or off in response to a first control signal;
    a signal conditioner, operatively coupled to the switch logic and to the group of microphones, the signal conditioner operative to receive outputs from each microphone of the group of microphones;
    voice recognition logic, operatively coupled to the signal conditioner; and
    a surface compensator, operatively coupled to the switch logic and to the signal conditioner, the surface compensator operative to:
        determine that a first microphone, of the group of microphones, is impeded by a surface that is in contact with the apparatus; and
        turn off the first microphone by sending the first control signal to the switch logic.

10. The apparatus of claim 9, further comprising:
    a plurality of sensors, operatively coupled to the surface compensator.

11. The apparatus of claim 10, further comprising:
    a vibrator, operatively coupled to the surface compensator;
    an accelerometer operatively coupled to the surface compensator, wherein the accelerometer is one sensor of the plurality of sensors; and
    wherein the surface compensator is operative to detect a surface in contact with the apparatus by:
        actuating the vibrator; and
        obtaining data from an accelerometer where the data exhibits a signature of the surface's surface type.

12. The apparatus of claim 11, wherein the surface compensator is operative to:
    select signal conditioning parameters based on the signature of the surface's surface type; and
    adjust the signal conditioner with the selected signal conditioning parameters.

13. The apparatus of claim 9, further comprising:
    changeover switch logic, operatively coupled to the switch logic; and
    a beamformer, operatively coupled to the changeover switch logic and to the signal conditioner, the beamformer operative to receive and beamform microphone outputs from the changeover switch logic to create a virtual microphone and to provide at least one voice recognition channel from the virtual microphone to the signal conditioner.

14. The apparatus of claim 13, wherein the surface compensator is operatively coupled to changeover switch logic, and wherein the surface compensator is operative to send a second control signal to the changeover switch logic to control the changeover switch logic to switch each microphone of the group of microphones either to the beamformer or to the signal conditioner.

15. The apparatus of claim 10, further comprising:
a 3D gyroscope wherein the 3D gyroscope is one of the plurality of sensors;
and wherein the surface compensator is operative to:
determine orientation of the apparatus by obtaining 3D gyroscope data; and
determine that the first microphone, of the group of microphones, is impeded by the surface based on the orientation of the apparatus and the first microphone's know position in the apparatus.

16. The apparatus of claim 9, wherein the signal conditioner comprises a noise suppressor and a de-reverberator.

17. The apparatus of claim 9, further comprising:
global positioning system logic, operatively coupled to the surface compensator; and
wherein the surface compensator is operative to receive global positioning system data from the global positioning system logic and determine when the apparatus is in motion in a vehicle based on the global positioning system data.

18. The apparatus of claim 11, further comprising:
non-volatile, non-transitory memory, operatively coupled to the surface compensator; and
wherein the surface compensator is operative to:
access the memory to compare the observed signature of the surface's surface type to a table of stored predetermined signatures and select the signal condition parameters from the table based on a matching predetermined signature.

19. The method of claim 1, wherein the data obtained from the accelerometer includes at least a frequency distribution value and a signal level value.

20. The method of claim 3, wherein the at least one sensor comprises one or more of a photosensor, a proximity sensor, a gyroscope, a vibrator, or the accelerometer.

* * * * *